United States Patent [19]

Pfister et al.

[11] 3,951,618
[45] Apr. 20, 1976

[54] METHOD OF USE OF, AND COMPOSITIONS CONTAINING, DISUBSTITUTED XANTHONE CARBOXYLIC ACID COMPOUNDS

[75] Inventors: Jurg R. Pfister, Los Altos; Ian T. Harrison; John H. Fried, both of Palo Alto, all of Calif.

[73] Assignee: Syntex (U.S.A.) Inc., Palo Alto, Calif.

[22] Filed: Jan. 20, 1975

[21] Appl. No.: 542,477

Related U.S. Application Data

[62] Division of Ser. No. 450,351, March 12, 1974, Pat. No. 3,886,181, which is a division of Ser. No. 217,300, Jan. 12, 1972, Pat. No. 3,821,251.

[52] U.S. Cl. ............................................. 424/283
[51] Int. Cl.² ....................................... A61K 31/35
[58] Field of Search .................................. 424/283

[56] References Cited
UNITED STATES PATENTS

| | | | |
|---|---|---|---|
| 3,706,768 | 12/1972 | Bays | 424/283 |
| 3,849,565 | 11/1974 | Pfister et al. | 424/283 |
| 3,864,493 | 2/1975 | Cairns et al. | 424/283 |
| 3,873,714 | 3/1975 | Pfister et al. | 424/283 |
| 3,885,038 | 5/1975 | Pfister et al. | 424/283 |

*Primary Examiner*—Norman A. Drezin
*Attorney, Agent, or Firm*—Gerard A. Blaufarb; Walter H. Dreger; William B. Walker

[57] ABSTRACT

Compositions containing and methods employing, as the essential ingredient, novel disubstituted xanthone carboxylic acid compounds which are useful in the treatment of allergic conditions. Methods for preparing these compounds and compositions and intermediates therein are also disclosed. 5-Methylthio-7-isopropoxyxanthone-2-carboxylic acid and 5,7-di-(methylthio)xanthone-2-carboxylic acid are illustrated as representative compounds.

56 Claims, No Drawings

METHOD OF USE OF, AND COMPOSITIONS CONTAINING, DISUBSTITUTED XANTHONE CARBOXYLIC ACID COMPOUNDS

This is a division of application Ser. No. 450,351, filed March 12, 1974, which is in turn a division of appliction Ser. No. 217,300, filed January 12, 1972, now U.S. Pat. No. 3,821,251.

The present invention is directed to novel disubstituted xanthone carboxylic acid compounds and to compositions containing and methods utilizing these compounds as the essential ingredient in the treatment of symptoms associated with allergic manifestations, for example, asthmatic conditions.

In a first aspect, the present invention relates to novel C-5,7 disubstituted xanthone-2-carboxylic acid compounds selected from those represented by the following formulas:

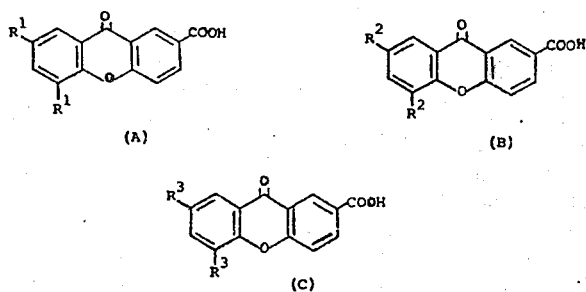

and the pharmaceutically acceptable, non-toxic esters, amides, and salts thereof;
wherein
each $R^1$ group is lower alkylthio;
one $R^2$ group is lower alkylthio and the other is lower alkyl; and
one $R^3$ group is lower alkylthio and the other is lower alkoxy.

Thus included within the scope of the present invention are the 5,7-di(lower alkylthio)xanthone-2-carboxylic acid compounds, 5-(lower alkylthio)-7-lower alkylxanthone-2-carboxylic acid compounds, 5-lower alkyl-7-(lower alkylthio)xanthone-2-carboxylic acid compounds, 5-(lower alkylthio)-7-lower alkoxyxanthone- 2-carboxylic acid compounds, and 5-lower alkoxy-7-(lower alkylthio)xanthone-2-carboxylic acid compounds, represented respectively by the following formulas:

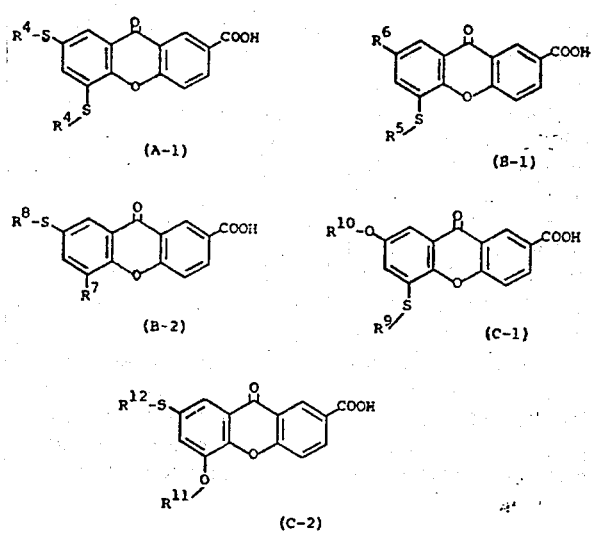

and the pharmaceutically acceptable, non-toxic esters, amides, and salts thereof; wherein each $R^4$, $R^5$, $R^6$, $R^7$, $R^8$, $R^9$, $R^{10}$, $R^{11}$, and $R^{12}$ is lower alkyl.

In a second aspect, the present invention is directed to a method useful for relieving symptoms associated with allergic manifestations such as are brought about by antigen-antibody (allergic) reactions. In the relief of these symptoms, the method hereof serves to inhibit the effects of the allergic reaction when administered in an effective amount. While not intending to be bound by any theoretical mechanism of action, the method hereof is believed to operate by inhibiting the release and/or the action of toxic products, e.g. histamine, 5-hydroxytryptamine, slow releasing substance (SRS-A), and others, which are produced as a result of a combination of specific antibody and antigen (allergic reaction). These properties make the subject compounds particularly useful in the treatment of various allergic conditions.

The compounds of the present invention are also smooth muscle relaxants, e.g. bronchial dilators, and are therefore useful in the treatment of conditions in which such agents may be indicated, as for instance; in the treatment of bronchio constriction. The compounds of the present invention are also vasodilators and are therefore useful in the treatment of conditions in which such agents may be indicated, as for instance, in renal and cardiac disorders.

This aspect of the present invention thus relates to a method useful for inhibiting the effects of the allergic reaction which comprises administering an effective amount of a compound selected from those represented above (A, B, and C), or a pharmaceutically acceptable non-toxic composition incorporating said acids, esters, amides or salts as an essential ingredient.

The present invention, in a third aspect, is directed to pharmaceutical compositions useful for inhibiting the effects of the allergic reaction comprising an effective amount of a compound selected from those represented above (A, B, and C), in admixture with a pharmaceutically acceptable non-toxic carrier.

In the practice of the method of the present invention, an effective amount of a compound of the present invention or pharmaceutical compositions thereof, as defined above, is administered via any of the usual and acceptable methods known in the art, either singly or in combination with another compound or compounds of the present invention or other pharmaceutical agents, such as antibiotics, hormonal agents, and so forth. These compounds or compositions can thus be administered orally, topically, parenterally, or by inhalation and in the form of either solid, liquid, or gaseous dosages including tablets, suspensions, and aerosols, as discussed in more detail hereinafter. The administration can be conducted in single unit dosage form with continuous therapy or in single dose therapy ad libitum. In the preferred embodiments, the method of the present invention is practiced when relief of symptoms is specifically required, or perhaps, imminent; however, the method hereof is also usefully practiced as continuous or prophylactic treatment.

In view of the foregoing as well as in consideration of the degree or severity of the condition being treated, age of subject, and so forth, all of which factors being determinable by routine experimentation by one skilled in the art; the effective dosage in accordance herewith can vary over a wide range. Generally, an effective amount ranges from about 0.005 to about 100 mg. per kg. of body weight per day and preferably from about 0.01 to about 100 mg. per kg. of body weight per day. In alternate terms, an effective amount in accordance herewith generally ranges from about 0.5 to about 7000 mg. per day per subject.

Useful pharmaceutical carriers for the preparation of the compositions hereof, can be solids, liquids, or gases. Thus, the compositions can take the form of tablets, pills, capsules, powders, sustained release formulations, solutions, suspensions, elixirs, aerosols, and the like. The carriers can be selected from the various oils including those of petroleum, animal, vegetable, or synthetic origin, for example, peanut oil, soybean oil, mineral oil, sesame oil, and the like. Water, saline, aqueous dextrose, and glycols are preferred liquid carriers, particularly for injectable solutions. Suitable pharmaceutical excipients include starch, cellulose, talc, glucose, lactose, sucrose, gelatin, malt, rice, flour, chalk, silica gel, margnesium stearate, sodium stearate, glyceryl monostearate, sodium chloride, dried skim milk, glycerol, propylene glycol, water, ethanol, and the like. Suitable pharmaceutical carriers and their formulation are described in "Remingtons Pharmaceutical Sciences" by E. W. Martin. Such compositions will, in any event, contain an effective amount of the active compound together with a suitable amount of carrier so as to prepare the proper dosage form for proper administration to the host.

The compounds of the present invention demonstrate activity as inhibitors of the effects of the allergic reaction as measured by tests indicative of such activity involving passive cutaneous anaphylaxis as substantially described, for example, by J. Goose et al., *Immunology*, 16, 749 (1969).

Certain of the compounds of the present invention can be prepared in accordance with the following reaction sequence:

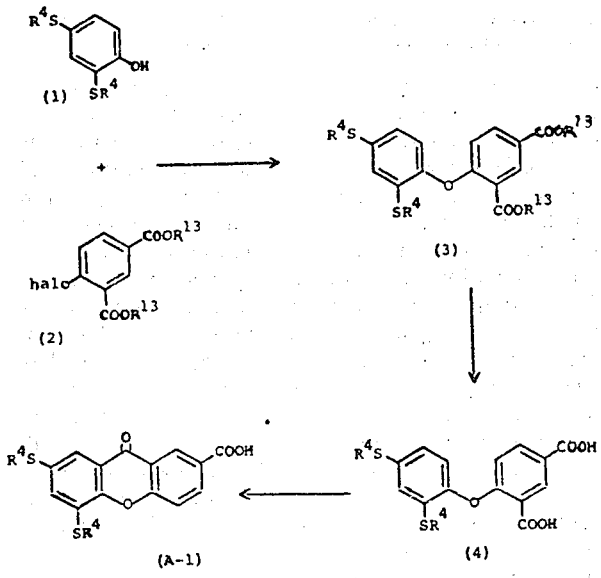

wherein each $R^4$ is as above defined, halo is bromo, chloro, fluoro, or iodo, preferably bromo; and $R^{13}$ is lower alkyl, preferably methyl.

With reference to the above reaction sequence, an ortho, para disubstituted ($SR^4$) phenol (1) is condensed with the 1,3-dicarbo(lower)alkoxy-4-halobenzene compound (2) in the presence of cuprous oxide optionally in organic liquid reaction medium, preferably an organic amide such as dimethyl acetamide, dimethylformamide, N-methylpyrrolidone, tetramethylurea, and so forth, to prepare the corresponding 1,3-dicarbo(lower)alkoxy-4-(o,p-disubstituted phenyloxy)-benzene compound (3).

The reaction is preferbly conducted in an inert organic reaction medium, such as those listed above, or suitable mixtures of one or more of such media. The reaction is further conducted at temperatures ranging from about 80° to about 220°C, preferably from about 120° to 200°C, and for a period of time sufficient to complete the reaction, ranging from about 2 hours to about 24 hours.

The reaction consumes the reactants on the basis of one mole of the substituted phenol per mole of the dicarbo(lower)-carboxyhalobenzene per half mole of cuprous oxide. However, the amounts of the reactants to be employed are not critical, some of the desired compound (3) being obtained when employing any proportions thereof. In the preferred embodiments, the reaction is conducted by reacting from about one to about three moles of the substituted phenol compound with about from 1 to about 1.2 moles of the dicarbo(lower)carboxyhalobenzene compound in the presence of from about 0.5 to about 0.6 moles of the cuprous oxide. The inert organic reaction medium, if employed, is used in solvent amounts.

Thereafter, the prepared compound (3) is base hydrolyzed to give the corresponding 1,3-dicarboxy-4-(o,p-disubstituted phenyloxy)-benzene (4). The base hydrolysis conditions can be any employed conventionally in the art. Generally, the hydrolysis reaction is conducted using an alkali metal hydroxide at about 50° to about 90°C and for a period of time sufficient to complete the reaction, ranging from about 15 minutes to about 60 minutes, preferably in the presence of inert organic reaction media such as those normally employed in organic chemical reactions of this type, e.g. aqueous alkanol solution. Although two moles of base are required per mole of compound (3), the amounts employed are not critical to produce the desired hydrolysis. Preferably from about three to about five moles of base are employed per mole of compound (3) and the reaction medium, if employed, is used in solvent amounts.

The thus prepared diacid compound (4) is then cyclized with phosphoryl chloride, thionyl chloride, sulfuric acid, hydrogen fluoride, or preferably, polyphosphoric acid (PPA), to give the corresponding 5,7-di(-lower alkylthio)-xanthone-2-carboxylic acid compound (A-1). The reaction is preferably, but optionally, conducted in an inert organic reaction medium including those usually employed in organic chemical reactions, such as dimethylsulfoxide, sulfolane, benzene, toluene, and so forth. The reaction is further conducted at temperatures ranging from about 60° to about 180°C, and for a period of time sufficient to complete the reaction ranging from about 15 minutes to about 90 minutes.

Although the reaction consumes the reactants on the basis of one mole of compound (4) per mole of cyclizing reagent, the reaction can be performed using any proportions of reactants. In the preferred embodiments, however, the reaction is conducted using from about 20 to about 50 moles of the cyclizing reagent per mole of starting compound (4).

The acid esters of the xanthone-2-carboxylic acids hereof are prepared by treatment with ethereal diazoalkane or with the desired lower alkanol in the presence of acid catalyst.

Certain of the compounds of the present invention can be prepared in accordance with the following reaction sequence:

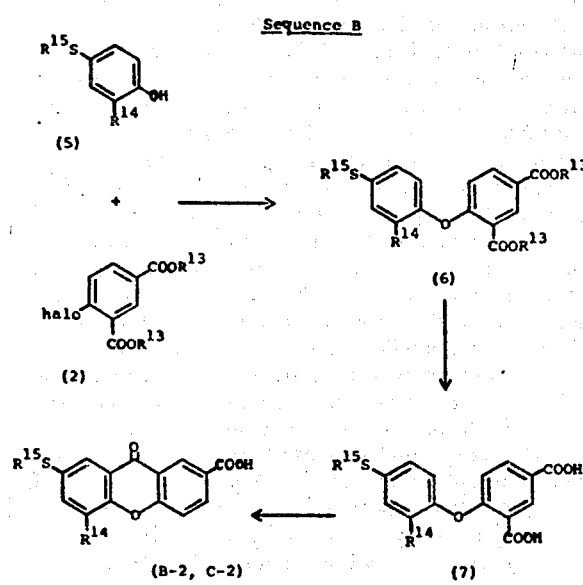

wherein each of halo and $R^{13}$ is as above defined; $R^{14}$ is lower alkyl or lower alkoxy; and $R^{15}$ is lower alkyl.

Certain of the compounds of the present invention can be prepared in accordance with the following reaction sequence:

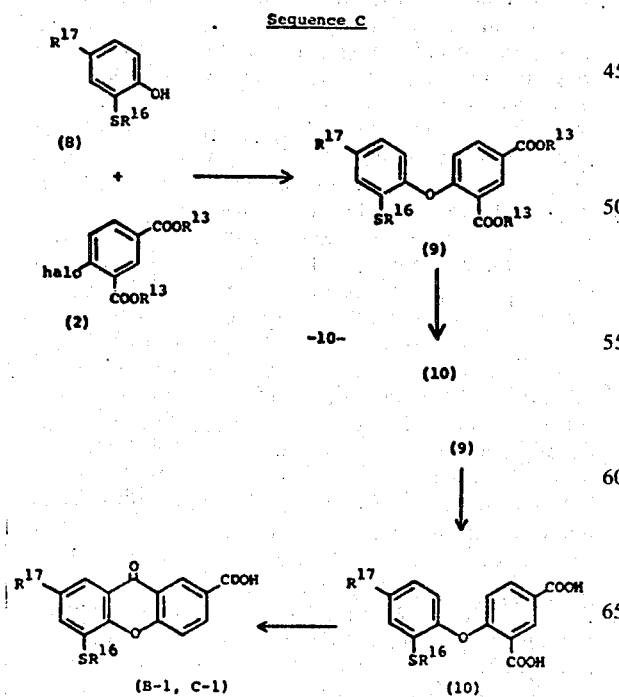

wherein each of halo and $R^{13}$ is as above defined; $R^{16}$ is lower alkyl; and $R^{17}$ is lower alkyl or lower alkoxy.

With reference to the above reaction Sequence B and C, the 5-lower alkyl- or -lower alkoxy-7-lower alkylthio compounds (B-2, C-2) and corresponding 5-lower alkylthio-7-lower alkyl- or -lower alkoxy compounds (B-1, C-1) are prepared as described above in Sequence A for compounds 1 → A-1.

Further methods by which certain of the compounds of the present invention can be prepared are as set forth in the following reaction sequence:

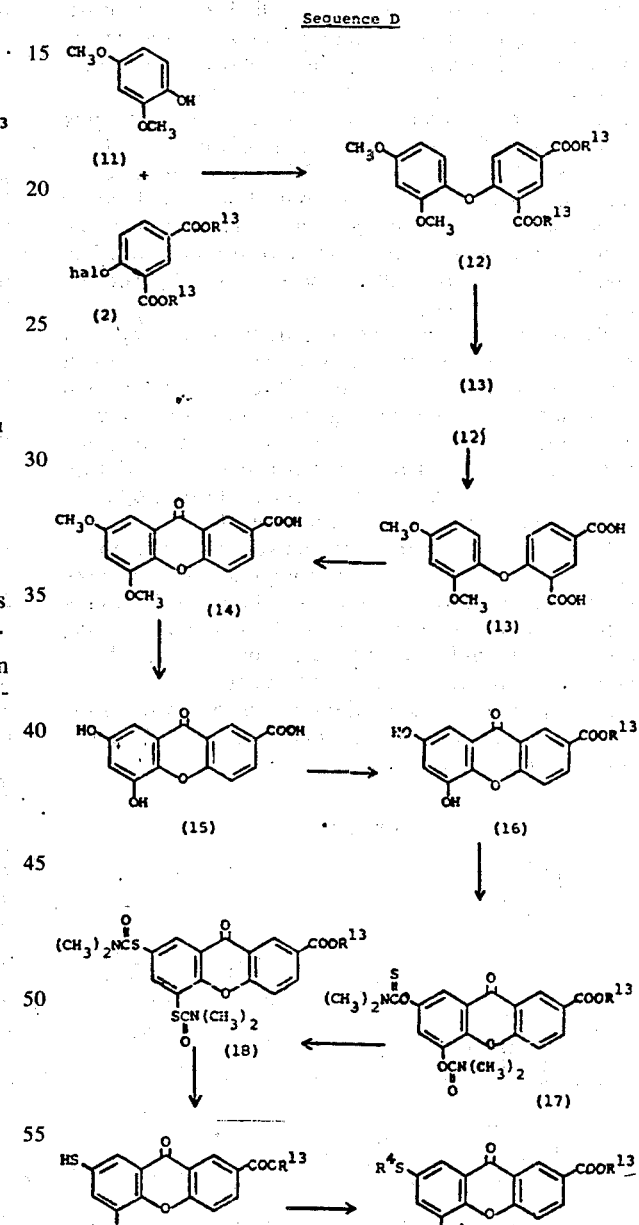

wherein each of halo, $R^4$ and $R^{13}$ is as above defined.

With reference to the above reaction sequence, the 5,7-dihydroxyxanthone-2-carboxylic acid esters (16) are prepared as described above in Sequence A for compounds 1 → A-1, including the step (14 → 15) of hydrolyzing the methyl ethers with hydrobromic or hydroiodic acid and acetic acid, preferably at temperatures of from about 100° to about 160°C, followed by conventional esterification as with a lower alkanol with a trace of sulfuric acid at reflux. Thereafter, compounds (16) are treated with a dialkylthiocarbamoyl chloride, such as dimethylthiocarbamoyl chloride, in the presence of base, such as an alkali metal hydride, and in organic liquid reaction media, preferably an organic amide such as those listed above with respect to reaction (1 + 2 → 3) to afford the products (17). The reaction is conducted at temperatures ranging from about 20° to about 100°C, preferably from 60° to about 80°C and for a period of time sufficient to complete the reaction, ranging from about one hour to about six hours. In the preferred embodiments, the reaction is conducted by reaction of from about 2.2 to about 3.0 moles of dialkylthiocarbamoyl chloride per mole of compound (16).

The product compounds (17) are then rearranged by reaction at a temperature of from about 200° to about 250°C, preferably from about 220° to about 230°C, and for a period of time ranging from about one hour to about eight hours and in the presence of organic medium such as sulfolane, nitrobenzene, triethyleneglycol, and so forth, which is preferably employed in solvent amounts, to give compounds (18).

Compounds (18) are then converted to the corresponding 5,7-dimercapto acid compounds (19) by base hydrolysis such as those described above for the preparation of compounds (4) from (3). Compounds (19) are alkylated with alkyl halide to give (20) which are conventionally hydrolyzed to the acids (A-1).

An alternative basic method by which certain of the compounds hereof can be prepared, as depicted above, is depicted as follows:

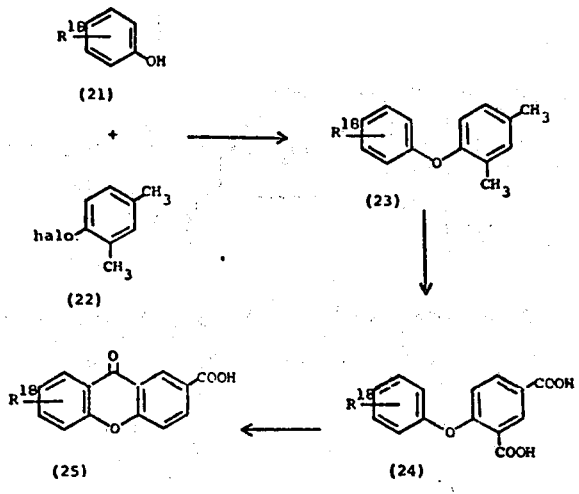

Sequence E wherein halo is as above defined and $R^{18}$ at ortho or para or both positions is lower alkoxy.

With reference to Sequence E, an appropriate phenol (21) is treated with 1,3-dimethyl-4-halo- (preferably iodo) benzene (22), as described above, to prepare the corresponding 1,3-dimethyl-4-phenyloxy benzene (23). This compound is then oxidized such as with potassium permanganate in aqueous t-butanol to give (24). This compound is then cyclized, as described above, to give the corresponding xanthone-2-carboxylic acid (25) which can be treated variously as described above, to prepare certain of the compounds of the present invention.

The starting compounds for use in the present invention are known and can be prepared by processes known per se. Thus, the 1,3-dicarbo(lower)alkoxy-4-halobenzene starting compounds (2) are conveniently prepared by oxidizing 1,3-dimethyl-4-halobenzene (4-halo-m-xylene) with potassium permanganate, as described above (23 → 24), followed by conventional esterification. The o,p-diloweralkylthiophenol compounds (1) are conveniently prepared by treating o-hydroxybenzoic acid with excess chlorosulfonic acid to give the corresponding o-hydroxy-m,m-di(chlorosulfonyl)-benzoic acid. This is reduced to the corresponding dimercapto compound with zinc and hydrogen chloride in acetic acid. The resultant compound is dialkylated with lower alkyl halide and potassium carbonate in dimethylformamide or with dialkylsulfate in aqueous sodium hydroxide to give o-alkoxy-m,m-di(alkylthio)-benzoic acid. The latter is decarboxylated with heating in the presence of copper and quinoline and the resultant compound selectively hydrolyzed with pyridine hydrochloride or with hydrogen bromide in acetic acid to give the o,p-di(lower alkylthio)-phenol.

The o,p-dialkoxyphenol starting compounds, i.e. (II), are prepared by treating o,p-dihydroxyacetophenone with an appropriate alkyl halide and potassium carbonate in dimethylformamide to give the corresponding dialkoxy compound. The latter is treated under Baeyer-Villiger conditions with peracid, e.g. peracetic or m-chloroperbenzoic acid, in chloroform containing p-toluenesulfonic acid to give 1-acetoxy-2,4-dialkoxybenzene. The latter is hydrolyzed to give the o,o-diloweralkoxyphenol compounds.

The o-alkyl or -alkoxy-p-alkylthiophenol starting compounds, i.e. (5), are conveniently prepared by treating an o-alkyl or -alkoxyphenol with chlorosulfonic acid in chloroform, followed by reduction with zinc-HCl in acetic acid, followed by alkylation all as described above (cf. preparation of 1) or by treatment of an o-alkyl or -alkoxyphenol with dialkylsulfoxide and gaseous hydrogen chloride to give the corresponding 3-alkyl or -alkoxy-4-hydroxybenzene dialkylsulfonium chloride. The latter is heated to give the corresponding o-alkyl or -alkoxy-p-alkylthiophenol product.

The corresponding o-alkylthio-p-alkyl or -alkoxyphenol starting compounds, i.e. (8), are prepared by treating an p-alkyl or -alkoxyphenol under Friedel-Crafts conditions to give the corresponding o-acetyl compound. This is oxidized to o-hydroxy-m-alkyl or -alkoxybenzoic acid which when treated with chlorosulfonic acid, followed by reduction, alkylation, and decarboxylation, all as described above, provides the desired compounds.

The acid esters of the xanthone-2-carboxylic acids hereof are prepared as described above (e.g. 15 → 16) upon treatment of the acid with ethereal diazoalkane such as diazomethane and diazoethane or with the desired lower alkyl iodide in the presence of lithium carbonate at room temperature or with the desired lower alkanol in the presence of a trace of sulfuric acid at reflux. The glycerol esters are prepared by treating the acid with thionyl chloride followed by treatment with a suitably protected ethylene glycol or propylene glycol (e.g. solketal) in pyridine, and hydrolyzing the protecting group of the ester thus formed with dilute acid.

The amides of the xanthone-2-carboxylic acids hereof are prepared by treatment of the acids with thionyl chloride followed by treatment with anhydrous ammonia, alkyl amine, dialkyl amine, dialkylaminoalkylamine, or phenethylamine.

The salts of the xanthone-2-carboxylic acids hereof are prepared by treating the corresponding acids with pharmaceutically acceptable base. Representative salts derived from such pharmaceutically acceptable bases include the sodium, potassium, lithium, ammonia, calcium, magnesium, ferrous, feric, zinc, manganous, aluminum, manganic, trimethylamine, triethylamine, tripropylamine, β-(dimethylamino)ethanol, triethanolamine, β-(diethylamino)ethanol, arginine, lysine, histidine, N-ethylpiperidine, hydrabamine, choline, betaine, ethylenediamine, glucosamine, methyl glucamine, theobromine, purines, piperazine, piperidine, polyamine resins, caffeine, procaine salts. The reaction is conducted in an aqueous solution, alone or in combination with an inert, water miscible organic solvent, at a temperature of from abut 0°C to about 100°C, preferably at room temperature. Typical inert, water miscible organic solvents include methanol, ethanol, isopropanol, butanol, acetone, dioxane, or tetrahydrofuran. When divalent metal salts are prepared, such as the calcium salts or magnesium salts of the acids, the free acid starting material is treated with about ½ molar equivalent of pharmaceutically acceptable base. When the aluminum salts of the acids are prepared, about ⅓ molar equivalent of the pharmaceutically acceptable base are employed.

In the preferred embodiment of the present invention, the calcium salts and magnesium salts of the acids are prepared by treating the corresponding sodium or potassium salts of the acids with at least ½ molar equivalent of calcium chloride or magnesium chloride, respectively, in an aqueous solution, alone or in combination with an inert water miscible organic solvent, at a temperature of from about 20°C to about 100°C.

In the preferred embodiment of the present invention, the aluminum salts of the acids are prepared by treating the acids with at least ⅓ molar equivalent of an aluminum alkoxide, such as aluminum triethoxide, aluminum tripropoxide, and the like, in a hydrocarbon solvent, such as benzene, xylene, cyclohexane, and the like, at a temperature of from about 20°C to about 115°C.

In the present specification and claims, by the term "lower alkyl" is intended a lower alkyl group containing one to five carbon atoms including straight and branched chain groups and cyclic alkyl groups, for example, methyl, ethyl, n-propyl, isopropyl, n-butyl, isobutyl, sec-butyl, t-butyl, n-pentyl, isopentyl, sec-pentyl, t-pentyl, cyclopropyl, cyclobutyl, and cyclopentyl. By the term "lower alkoxy" is intended the group "O-lower alkyl" wherein "lower alkyl" is as defined above. "Lower alkylthio" is the group "s-lower alkyl" wherein "lower alkyl" is as defined above.

By the term "pharmaceutically acceptable, non-toxic esters, amides, and salts" is respectively intended an alkyl or glycerol ester: an unsubstituted, monoalkyl, dialkyl, dialkylaminoalkyl, alkoxyalkyl, or phenethyl substituted amide and a salt as defined above.

The nomenclature herein is employed in accordance with *Chemical Abstracts*, 56, Subject Index (1962, January-June).

The following examples illustrate the method by which the present invention can be practiced.

EXAMPLE 1

A. A mixture of 4.188 g. of 1,3-dicarbomethoxy-4-bromobenzene, 3.8 g. of o,p-di(methylthio)phenol, 1.32 g. of cuprous oxide in 20 ml. of dimethylacetamide is heated to 160°C and maintained thereat with stirring and under a nitrogen atmosphere. After monitoring via tlc indicates the reaction is substantially complete, the reaction mixture is diluted with water and extracted with diethylether.methylene chloride (3:1). The extracts are chromatographed on 150 g. of alumina and the uniform fractions combined to give 1,3-dicarbomethoxy-4-(o,p-di(methylthio)phenyloxy)-benzene.

B. 1,3-Dicarbomethoxy-4-(o,p-di(methylthio)-phenyloxy)-benzene (3.0 g.) is combined with 150 ml of 5% potassium hydroxide in methanol. The resultant mixture is refluxed for one hour after which time it is acidified, cooled, and filtered, to give 1,3-dicarboxy-4-(o,p-di(methylthio)phenyloxy)-benzene.

C. 2.0 grams of 1,3-dicarboxy-4-(o,p-di(methylthio)-phenyloxy)-benzene in 20 ml. of concentrated sulfuric acid is stirred at 80°C for one hour. After this time, the reaction mixture is poured into 200 ml. of ice water and the resultant mixture is heated on a steam bath for 15 minutes. The mixture is cooled and filtered with the precipitate being washed with water and then recrystallized from acetic acid to give 5,7-di(methylthio)-xanthone-2-carboxylic acid.

The foregoing procedure can be practiced using an alternative 1,3-dicarboloweralkoxy-4-halo starting compound, such as 1,3-dicarbomethoxy-4-chloro-(or iodo)-benzene, 1,3-dicarboethoxy-4-fluoro-benzene, 1,3-dicarboethoxy-4-bromo-benzene, and the like, with similar results. Likewise, the foregoing procedure can be practiced using an alternate 2,4-dilower alkylthiophenol starting compound to prepare the corresponding 5,7-di(lower alkylthio)-xanthone-2-carobxylic acid, e.g.

5,7-di(ethylthio)-xanthone-2-carboxylic acid,
5,7-di(n-propylthio)-xanthone-2-carboxylic acid,
5,7-di(isopropylthio)-xanthone-2-carboxylic acid,
5,7-di(n-butylthio)-xanthone-2-carboxylic acid,
5,7-di(isobutylthio)-xanthone-2-carboxylic acid,
5,7-di(sec-butylthio)-xanthone-2-carboxylic acid,
5,7-di(t-butylthio)-xanthone-2-carboxylic acid,
5,7-di(n-pentylthio)-xanthone-2-carboxylic acid,
5,7-di(cyclopropylthio)-xanthone-2-carboxylic acid,
5,7-di(cyclobutylthio)-xanthone-2-carboxylic acid, and
5,7-di(cyclopentylthio)-xanthone-2-carboxylic acid.

EXAMPLE 2

The compounds 5-loweralkyl or -loweralkoxy-7-(lower-alkylthio)-xanthone-2-carboxylic acid, e.g.:

5-methyl-7-(methylthio)-xanthone-2-carboxylic acid,
5-ethyl-7-(methylthio)-xanthone-2-carboxylic acid,
5-n-propyl-7-(methylthio)-xanthone-2-carboxylic acid,
5-isopropyl-7-(methylthio)-xanthone-2-carboxylic acid, 5-n-butyl-7-(methylthio)-xanthone-2-carboxylic acid,
5-isobutyl-7-(methylthio)-xanthone-2-carboxylic acid,
5-sec-butyl-7-(methylthio)-xanthone-2-carboxylic acid,
5-t-butyl-7-(methylthio)-xanthone-2-carboxylic acid,
5-n-pentyl-7-(methylthio)-xanthone-2-carboxylic acid,
5-isopentyl-7-(methylthio)-xanthone-2-carboxylic acid,
5-cyclopentyl-7-(methylthio)-xanthone-2-carboxylic acid,
5-methoxy-7-(methylthio)-xanthone-2-carboxylic acid,
5-ethoxy-7-(methylthio)-xanthone-2-carboxylic acid,
5-n-propoxy-7-(methylthio)-xanthone-2-carboxylic acid,
5-isopropoxy-7-(methylthio)-xanthone-2-carboxylic acid,
5-n-butoxy-7-(methylthio)-xanthone-2-carboxylic acid,
5-isobutoxy-7-(methylthio)-xanthone-2-carboxylic acid,
5-sec-butoxy-7-(methylthio)-xanthone-2-carboxylic acid,
5-t-butoxy-7-(methylthio)-xanthone-2-carboxylic acid,
5-n-pentyloxy-7-(methylthio)-xanthone-2-carboxylic acid,
5-isopentyloxy-7-(methylthio)-xanthone-2-carboxylic acid,
5-cyclopentyloxy-7-(methylthio)-xanthone-2-carboxylic acid,
and the corresponding 5-substituted 22 compounds in each of the 7-ethylthio-, 7-n-propylthio-, 7-isopropylthio-, 7-n-butylthio-, 7-isobutylthio-, 7-sec-butylthio-, 7-t-butylthio-, 7-n-pentylthio-, 7-isopentylthio-, and 7-(cyclopentylthio)-xanthone-2-carboxylic acid series are prepared according to the procedures (A), (B) and (C) of Example 1.

EXAMPLE 3

Example 2 is repeated to prepare the 5-(lower alkylthio)-7-lower alkyl or -lower alkoxy-xanthone-2-carboxylic acid compounds, i.e.:
5-methylthio-7-methylxanthone-2-carboxylic acid,
5-methylthio-7-ethylxanthone-2-carboxylic acid,
5-methylthio-7-n-propylxanthone-2-carboxylic acid,
5-methylthio-7-isopropylxanthone-2-carboxylic acid,
5-methylthio-7-n-butylxanthone-2-carboxylic acid,
5-methylthio-7-isobutylxanthone-2-carboxylic acid,
5-methylthio-7-sec-butylxanthone-2-carboxylic acid,
5-methylthio-7-t-butylxanthone-2-carboxylic aicd,
5-methylthio-7-n-pentylxanthone-2-carboxylic acid,
5-methylthio-7-isopentylxanthone-2-carboxylic acid,
5-methylthio-7-cyclopentylxanthone-2-carboxylic acid,
5-methylthio-7-methoxyxanthone-2-carboxylic acid,
5-methylthio-7-ethoxyxanthone-2-carboxylic acid,
5-methylthio-7-n-propoxyxanthone-2-carboxylic acid,
5-methylthio-7-isopropoxyxanthone-2-carboxylic acid,
5-methylthio-7-n-butoxyxanthone-2-carboxylic acid,
5-methylthio-7-isobutoxyxanthone-2-carboxylic acid,
5-methylthio-7-sec-butoxyxanthone-2-carboxylic acid,
5-methylthio-7-t-butoxyxanthone-2-carboxylic acid,
5-methylthio-7-n-pentyloxyxanthone-2-carboxylic acid,
5-methylthio-7-isopentyloxyxanthone-2-carboxylic acid,
and
5-methylthio-7-cyclopentyloxyxanthone-2-carboxylic acid, and the corresponding total of 22 compounds in each of the 5-ethylthio-, 5-n-propyl-, 5-n-propylthio-, 5-isopropylthio-, 5-n-butylthio-, 5-isobutylthio-, 5-sec-butylthio-, 5-t-butylthio-, 5-n-pentylthio-, 5-isopentylthio-, and 5-(cyclopentylthio)-xanthone-2-carboxylic acid series.

EXAMPLE 4

The compound 5,7-dimethoxyxanthone-2-carboxylic acid is prepared from o,p-dimethoxyphenol according to the procedures (A), (B), and (C) of Example 1.

A mixture of 11 grams of 5,7-dimethoxyxanthone-2-carboxylic acid in 100 ml. of concentrated aqueous hydrogen iodide and 100 ml. of acetic acid is refluxed for four hours. After this time, the mixture is cooled, diluted with water, and filtered. The precipitate is washed and dried to give 5,7-dihydroxyxanthone-2-carboxylic acid.

Alternatively, the hydroxy compound can be prepared according to the procedure of Example 1.

A mixture of 4 g. of 5,7-dihydroxyxanthone-2-carboxylic acid, 10 g. of methyl iodide, and 10 g. of lithium carbonate in 50 ml. of dimethylformamide is stirred at room temperature for a period of 16 hours. After this period of time, the reaction mixture is poured into dilute hydrochloric acid-ice and the resultant mixture extracted with ethyl acetate. The extracts are filtered through alumina to give methyl 5,7-dihydroxyxanthone-[2-carboxylate which can be recrystallized from methanol.

To a solution of 6.2 g. of methyl 5,7-dihydroxyxanthone-2-carboxylate in 100 ml. of dimethylformamide are added 2 g. of sodium hydride. The mixture is stirred for ten minutes at room temperature under nitrogen. Dimethylthiocarbamoyl chloride (6 g.) is then added thereto and the resultant mixture stirred at 70°C for six hours and then at room temperature for 16 hours. The mixture is then poured into 200 ml. of water containing 1 ml. of acetic acid, the resultant mixture is filtered and the solid dried to give methyl 5,7-di(dimethylthiocarbamoyloxy)-xanthone-2-carboxylate.

Methyl 5,7-di(dimethylthiocarbamoyloxy)-xanthone-2-carboxylate (8 g.) in 150 ml. of sulfolane is stirred at 230°C under nitrogen. After a total of six hours under these conditions, tlc indicates the absence of starting material. The mixture is cooled to 80°C and 150 ml. of hot water are slowly added. The mixture is then cooled and the filtered solid washed with water and dried to give methyl 5,7-di(dimethylcarbamoylthio)-xanthone-2-carboxylate.

Methyl 5,7-di(dimethylcarbamoylthio)-xanthone-2-carboxylate (7.5 g.), 10 g. of potassium hydroxide and 250 ml. of 80% aqueous ethanol is refluxed for one hour. After this time, 250 ml. of water are added and the mixture is treated with charcoal, filtered, and acidified. The product is filtered off and dried to give 5,7-dimercaptoxanthone-2-carboxylic acid.

A mixture of 4 g. of 5,7-dimercaptoxanthone-2-carboxylic acid, 10 g. of methyl iodide, and 10 g. of lithium carbonate in 50 ml. of dimethylformamide is stirred at room temperature for a period of 16 hours. After this period of time, the reaction mixture is poured into dilute hydrochloric acid-ice and the resultant mixture extracted wit ethyl acetate. The extracts are filtered through alumina to give methyl 5,7-di(methylthio)-xanthone-2-carboxylate which can be recrystallized from methanol.

Methyl 5,7-di(methylthio)-xanthone-2-carboxylate (720 mg.), 75 ml. of ethanol, and 10 ml. of 5% sodium hydroxide are refluxed for 30 minutes. The mixture is cooled, partially evaporated and acidified. The precipitate is filtered off, washed and dried to give 5,7-di(methylthio)-xanthone-2-carboxylic acid which can be recrystallized from acetic acid.

In like manner, the following are prepared:
5,7-di(ethylthio)-xanthone-2-carboxylic acid,
5,7-di(n-propylthio)-xanthone-2-carboxylic acid,
5,7-di(isopropylthio)-xanthone-2-carboxylic acid,
5,7-di(butylthio)-xanthone-2-carboxylic acid,
5,7-di(pentylthio)-xanthone-2-carboxylic acid,
5,7-di(cyclopropylthio)-xanthene-2-carboxylic acid, and the like.

EXAMPLE 5

A mixture of three grams of 5,7-dimercaptoxanthone-2-carboxylic acid in 150 ml. of dimethylformamide, 5 ml. of methyl iodide and 5 ml. of potassium carbonate is stirred for 16 hours at 60°C. The mixture is then poured into dilute hydrochloric acid and the resultant mixture extracted with ethyl acetate. The extracts are chromatographed on alumina (methylene chloride) to give methyl 5,7-di(methylthio)-xanthone-2-carboxylate (i.e. methyl 5,7-di(thiomethoxy)-xanthone-2carboxylate which can be recrystallized from methylene chloride/methanol.

A mixture of 580 mg. of methyl 5,7-di(methylthio)-xanthone-2-carboxylate, 30 ml. of ethanol, 5 ml. of saturated sodium carbonate solution and 5 ml. of water is refluxed for one hour. The mixture is then cooled, acidified and the precipitate filtered off to give 5,7-di(-methylthio)-xanthone-2-carboxylic acid (i.e. 5,7-di(-thiomethoxy)-xanthone-2-carboxylic acid) as also prepared in the alternative method described in Example 1.

A mixture of 0.8 g. of 5,7-dimercaptoxanthone-2-carboxylic acid, 2 ml. of 2-bromopropane, and excess potassium carbonate in 50 ml. of dimethylformamide is stirred for 24 hours at 75°C. Dilute hydrochloric acid and ethanol are added, the solid filtered off and washed. The solid is saponified with sodium carbonate in aqueous methanol (30 minutes reflux). The alkaline solution is diluted with water, treated with charcoal, filtered, and acidified to give 5,7-di(isopropylthio)-xanthone-2-carboxylic acid which can be recrystallized from tetrahydrofuran/ethyl acetate.

The foregoing are useful as an alternative to the method of Example 1 for the preparation of the compounds hereof.

EXAMPLE 6

A mixture of 3 g. of 1,3-dicarboxy-4-(o,p-di(methylthio)-phenyloxy)-benzene, 75 ml. of polyphosphoric acid, and 75 ml. of sulfolane is stirred at 125°C for a period of two hours. After this time, the reaction mixture is poured into water, filtered and the precipitate washed. The precipitate is recrystallized from acetic acid (charcoal) to give 5,7-di(methylthio)-xanthone-2-carboxylic acid.

In a similar manner, the foregoing procedure can be practiced utilizing other o-, p-, o,p-lower alkylthiophenol starting compounds to prepare the corresponding products, for example:
5,7-di(methylthio)-xanthone-2-carboxylic acid,
5,7-di(ethylthio)-xanthone-2-carboxylic acid,
5,7-di(n-propylthio)-xanthone-2-carboxylic acid,
5,7-di(isopropylthio)-xanthone-2-carboxylic acid,
5,7-di(n-butylthio)-xanthone-2-carboxylic acid, and so forth.

EXAMPLE 7

A mixture of 4.5 grams of 5,7-di(methylthio)-xanthone-2-carboxylic acid, 10 g. of methyl iodide, and 10 g. of lithium carbonate in 75 ml. of dimethylformamide is stirred at room temperature for a period of 18 hours. After this period of time, the reaction mixture is poured into dilute hydrochloric acid-ice and the resultant precipitate is filtered off and washed to give methyl 5,7-di(methylthio)-xanthone-2-carboxylate.

The foregoing procedure is repeated using the alternate lower alkyl iodides so as to prepare the corresponding lower alkyl acid esters hereof, e.g.:
ethyl 5,7-di(methylthio)-xanthone-2-carboxylate,
n-propyl 5,7-di(methylthio)-xanthone-2-carboxylate,
isopropyl 5,7-di(methylthio)-xanthone-2-carboxylate,
n-propyl 5,7-di(methylthio)-xanthone-2-carboxylate,
isobutyl 5,7-di(methylthio)-xanthone-2-carboxylate,
sec-butyl 5,7-di(methylthio)-xanthone-2-carboxylate,
t-butyl 5,7-di-methylthio)-xanthone-2-carboxylate,
n-pentyl 5,7-di(methylthio)-xanthone-2-carboxylate, and so forth.

In like manner, the other xanthone-2-carboxylic acids hereof containing substituents at the C-5,7 positions, prepared as described above, can be converted to the corresponding acid esters, e.g.:
methyl 5,7-di(ethylthio)-xanthone-2-carboxylate,
ethyl 5-methylthio-7-isopropoxyxanthone-2-carboxylate,
n-propyl 5,7-dimercaptoxanthone-2-carboxylate,
methyl 5-ethyl-7-(ethylthio)-xanthone-2-carboxylate, and so forth.

The esters are also prepared by treating the acid with the appropriate lower alkanol under reflux and in the presence of acid to give, e.g.:
methyl 5,7-di(isopropylthio)-xanthone-2-carboxylate, and
ethyl 5,7-dimercaptexanthone-2-carboxylate.

EXAMPLE 8

To a solution of 10 g. of 5,7-di(methylthio)-xanthone-2-carboxylic acid in 200 ml. of ethanol is added the theoretical
amount of sodium hydroxide dissolved in 200 ml. of 90% ethanol. The reaction mixture is then concentrated in vacuum to give sodium 5,7-di(methylthio)-xanthone-2-carboxylate.

In a similar manner, the potassium and lithium salts are prepared. Similarly, by replacing the sodium salt by means of an appropriate metal salt reagent, e.g., calcium chloride, manganese chloride, and so forth, the other xanthone-2-carboxylic acid salts are prepared, e.g.:

magnesium 5,7-di(methylthio)-xanthone-2-carboxylate,
calcium 5,7-di(methylthio)-xanthone-2-carboxylate,
aluminum 5,7-di(methylthio)-xanthone-2-carboxylate,
ferrous 5,7-di(methylthio)-xanthone-2-carboxylate,
zinc 5,7-di(methylthio)-xanthone-2-carboxylate,
manganese 5,7-di(methylthio)-xanthone-2-carboxylate,
ferric 5,7-di(methylthio)-xanthone-2-carboxylate,
and so forth.

In a similar manner, the xanthone-2-carboxylic acid salts of the other C-5,7 disubstituted xanthone-2-carboxylic acids hereof are prepared, e.g.:

potassium 5,7-di(ethylthio)-xanthone-2-carboxylate,
sodium 5-isopropyl-7-methylthioxanthone-2-carboxylate,
potassium 5,7-di(isopropylthio)-xanthone-2-carboxylate,
sodium 5,7-di(cyclopropylthio)-xanthone-2-carboxylate, and so forth.

EXAMPLE 9

To a mixture of 50 milliliters of concentrated aqueous ammonia in 500 ml. of methanol there are added 20 g. of 5,7-di(methylthio)-xanthone-2-carboxylic acid. The resultant mixture is stirred for two hours and is then evaporated to dryness to give the ammonium salt of 5,7-di(methylthio)-xanthone-2-carboxylic acid.

A solution of 10 g. of 5,7-di(methylthio)-xanthone-2-carboxylic acid in 50 ml. of thionyl chloride is heated at reflux for one hour. Thereafter, the solution is evaporated to dryness to give the corresponding acid chloride to which is added a concentrated ethereal ammonia solution. The resultant solution is evaporated giving the 5,7-di(methylthio)-xanthone-2-carboxylic acid amide.

In like manner, the lower alkyl amides can be prepared using monoalkylamine or dialkylamine in lieu of ammonia in the above procedures. Thus prepared, are, e.g.:

5,7-di(ethylthio)-xanthone-2-carboxylic acid amide,
N-methyl 5,7-di(n-propylthio)-xanthone-2-carboxylic acid amide,
N,N-dimethyl 5-(methylthio)-7-methylxanthone-2-carboxylic acid amide,
N,N-diethyl 5,7-di(cyclopentylthio)-xanthone-2-carboxylic acid amide,
N,N-diethyl 5,7-di(t-butylthio)-xanthone-2-carboxylic acid amide,
N-ethyl 5-ethoxy-7-ethylthioxanthone-2-carboxylic acid amide,
N-n-propyl 5-propyl-7-(propylthio)-xanthone-2-carboxylic acid amide, and so forth.

EXAMPLE 10

To a mixture of 20 g. of procaine and 500 ml. of aqueous methanol are added 20 g. of 5,7-di(methylthio)-xanthone-2-carboxylic acid. The resultant mixture is stirred at room temperature for 16 hours. It is then evaporated under reduced pressure to give the procaine salt of 5,7-di(methylthio)-xanthone-2-carboxylic acid.

Similarly, the lysine, caffeine, and arginine salts thereof are obtained. In like manner, the e.g. procaine, lysine, caffeine, and arginine salts of the other C-5,7 disubstituted xanthone-2-carboxylic acids are obtained, e.g.:

the procaine salt of 5,7-di(ethylthio)-xanthone-2-carboxylic acid,
the caffeine salt of 5-(propylthio)-7-n-butoxyxanthone-2-carboxylic acid,
the lysine salt of 5,7-di(di-t-butylthio)-xanthone-2-carboxylic acid,
the procaine salt of 5-(sec-butylthio)-7-sec-butoxyxanthone-2-carboxylic acid, and
the arginine salt of 5,7-di(cyclobutylthio)-xanthone-2-carboxylic acid.

EXAMPLE 11

The following procedures illustrate the method by which the pharmaceutical compositions of the compounds hereof are prepared.

Sodium chloride (0.44 g.) is dissolved in 80 ml. of a (9.47 g/l. water) sodium hydrogen phosphate solution. A sodium dihydrogen phosphate (8.00 g/l. water) solution (20 ml.) is then added thereon. The resultant solution having a pH of 7.38 thereto. sterilized in an autoclave. This vehicle is then added to solid, dry 5,7-di(methylthio)-xanthone-2-carboxylic acid to give a preparation suitable for intravenous injection containing 2.5 mg. of 5,7-di(methylthio)-xanthone-[2-carboxylic acid per milliliter of total composition.

EXAMPLE 12

The following procedure illustrates a test procedure for the compounds hereof.

Normal female (Sprague-Dawley) rats of 150 to 200 grams each are passively sensitized intradermally by injection of rat anti-egg albumin reaginic sera. After 24 hours, each rat is challenged intravenously with 1 ml. of 0.5% Evans blue, 1 mg. egg albumin plus 10 mg. of 5,7-di(methylthio)-xanthone-2-carboxylic acid. Control rats receive no 5,7-di(methylthio)-xanthone-2-carboxylic acid. The dermal bluing is recorded 15 to 25 minutes later. The rats which receive the 5,7-di(methylthio)-xanthone-2-carboxylic acid exhibit a 100% inhibition of allergic reaction whereas the control rats exhibit no inhibition.

The above procedure is repeated using 5,7-di(methylthio)-xanthone-2-carboxylic acid, with similar results. The above procedure is repeated using oral administration, with similar results.

The C-5,7 disubstituted xanthone-2-carboxylic acid compounds are administered by gavage at a dose of 20 mg. per animal 15 minutes prior to challenge. Twenty to thirty minutes after challenge the degree of dermal bluing is read, with similar results.

Inhibition of reaginic antigen-antibody reactions in rats is regarded as representative of inhibition of human reaginic antigen-antibody reactions which occur during allergic episodes.

Subjects challenged by antigen inhalation are measured for the extent of provoked degree of asthma condition by changes in airway resistance on expiration. The subject compounds are administered as an aerosol by inhalation before antigen challenge. Prevention of asthmatic conditions upon the administration of the compounds is evidenced by a decrease in airway resistance and other, subjective improvements, e.g. reduced cough.

What is claimed is:

1. A method for inhibiting the symptoms of the asthmatic condition resulting from an antigen-antibody reaction in a host susceptible to said reaction which comprises administering to said host an effective amount of from about 0.005 to about 100 mg. per kg. of body weight per day sufficient to produce said inhibition of a compound represented by the formulas:

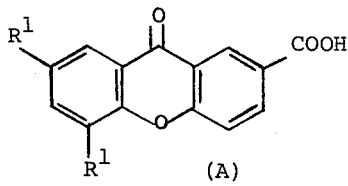
(A)

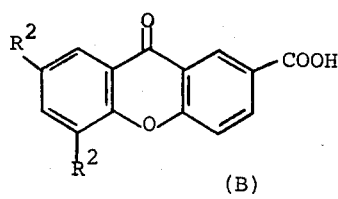
(B)

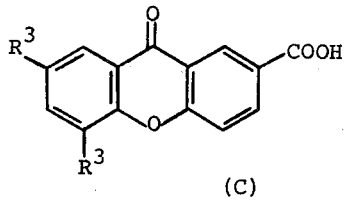
(C)

wherein
each $R^1$ group is lower alkylthio;
one $R^2$ group is lower alkylthio and the other is lower alkyl; and
one $R^3$ group is lower alkylthio and the other is lower alkoxy;
or a pharmaceutically acceptable non-toxic alkyl or glycerol ester, unsubstituted, monoalkyl, dialkyl, dialkylaminoalkyl, alkoxyalkyl, or phenethyl substituted amide, or salt thereof, wherein said alkyl and alkoxy groups each contain 1 to 5 carbon atoms.

2. The method according to claim 1 in which the compound is the compound of formula (A).

3. The method according to claim 2 in which the compound is the compound wherein each $R^1$ is methylthio; 5,7-di(methylthio)-xanthone-2-carboxylic acid.

4. The method according to claim 2 in which the compound is the compound wherein each $R^1$ is isopropylthio; 5,7-di(isopropylthio)-xanthone-2-carboxylic acid.

5. The method according to claim 1 in which the compound is the compound of formula (B).

6. The method according to claim 5 in which the compound is the compound of the formula:

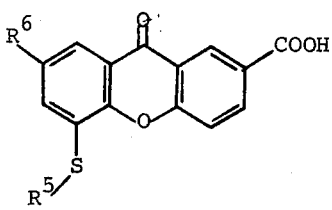

wherein each of $R^5$ and $R^6$ is the lower alkyl.

7. The method according to claim 6 in which the compound is the compound wherein $R^5$ is methyl.

8. The method according to claim 7 in which the compound is the compound wherein $R^6$ is isopropyl; 5-methylthio-7-isopropylxanthone-2-carboxylic acid.

9. The method according to claim 7 in which the compound is the compound wherein $R^6$ is n-pentyl; 5-methylthio-7-n-pentylxanthone-2-carboxylic acid.

10. The method according to claim 7 in which the compound is the compound wherein $R^6$ is isobutyl; 5-methylthio-7-isobutylxanthone-2-carboxylic acid.

11. The method according to claim 5 in which the compound is the compound of the formula:

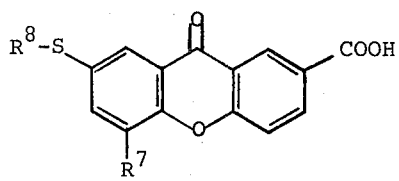

wherein each of $R^7$ and $R^8$ is lower alkyl.

12. The method according to claim 11 in which the compound is the compound wherein $R^8$ is methyl.

13. The method according to claim 12 in which the compound is the compound wherein $R^7$ is isopropyl; 5-isopropyl-7-(methylthio)-xanthone-2-carboxylic acid.

14. The method according to claim 12 in which the compound is the compound wherein $R^7$ is n-pentyl; 5-n-pentyl-7-(methylthio)-xanthone-2-carboxylic acid.

15. The method according to claim 12 in which the compound is the compound wherein $R^7$ is isobutyl; 5-isobutyl-7-(methylthio)-xanthone-2-carboxylic acid.

16. The method according to claim 1 in which the compound is the compound of formula (C).

17. The method according to claim 16 in which the compound is the compound of the formula:

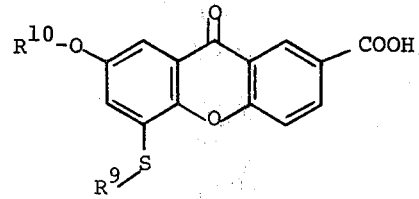

wherein each of $R^9$ and $R^{10}$ is lower alkyl.

18. The method according to claim 17 in which the compound is the compound wherein $R^9$ is methyl.

19. The method according to Claim 18 in which the compound is the compound wherein $R^{10}$ is isopropyl; 5-methylthio-7-isopropoxyxanthone-2-carboxylic acid.

20. The method according to claim 16 in which the compound is the compound of the formula:

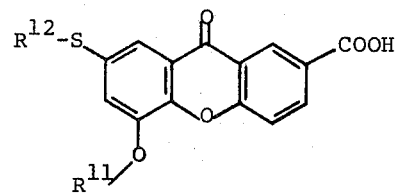

wherein each of $R^{11}$ and $R^{12}$ is lower alkyl.

21. The method according to claim 20 in which the compound is the compound wherein $R^{12}$ is methyl.

22. The method according to claim 21 in which the compound is the compound wherein $R^{11}$ is isopropyl; 5-isopropoxy-7-(methylthio)-xanthone-2-carboxylic acid.

23. The method according to claim 1 in which the compound is the sodium salt compound.

24. The method according to claim 23 in which the compound is the sodium salt compound of formula (A).

25. The method according to claim 23 in which the compound is the sodium salt compound of formula (B).

26. The method according to claim 23 in which the compound is the sodium salt compound of formula (C).

27. A composition for inhibiting the symptoms of the asthmatic condition resulting from an antigen-antibody reaction which comprises an effective amount sufficient to produce said inhibition of a compound represented by the formulas:

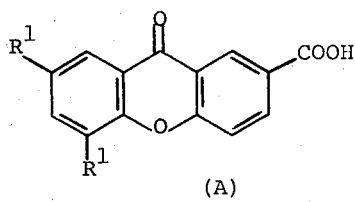

(A)

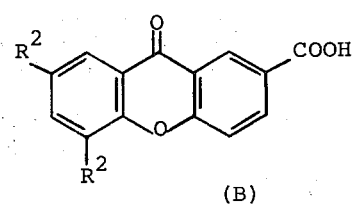

(B)

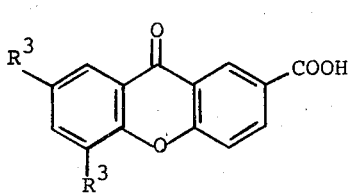

(C)

and the pharmaceutically acceptable, non-toxic esters, amides, and salts thereof;
wherein
each $R^1$ group is lower alkylthio;
one $R^2$ group is lower alkylthio and the other is lower alkyl; and
one $R^3$ group is lower alkylthio and the other is lower alkoxy;
or a pharmaceutically acceptable non-toxic alkyl or glycerol ester, unsubstituted, monoalkyl, dialkyl, dialkylaminoalkyl, alkoxyalkyl, or phenethyl substituted amide, or salt thereof, wherein said alkyl and alkoxy groups each contain 1 to 5 carbon atoms; in admixture with a pharmaceutically acceptable non-toxic carrier.

28. The composition according to claim 27 in which the compound is the compound of formula (A).

29. The composition according to claim 28 in which the compound is the compound wherein each $R^1$ is methylthio; 5,7-di(methylthio)-xanthone-2-carboxylic acid.

30. The composition according to claim 28 in which the compound is the compound wherein each $R^1$ is isopropylthio; 5,7-di(isopropylthio)-xanthone-2-carboxylic acid.

31. The composition according to claim 27 in which the compound is the compound of formula (B).

32. The composition according to claim 31 in which the compound is the compound of the formula:

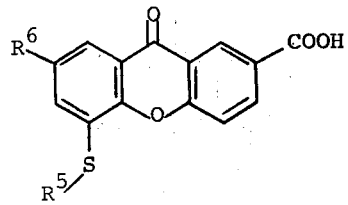

wherein each of $R^5$ and $R^6$ is lower alkyl.

33. The composition according to claim 32 in which the compound is the compound wherein $R^5$ is methyl.

34. The composition according to claim 33 in which the compound is the compound wherein $R^6$ is isopropyl; 5-methylthio-7-isopropylxanthone-2-carboxylic acid.

35. The composition according to claim 33 in which the compound is the compound wherein $R^6$ is n-pentyl; 5-methylthio-7-n-pentylxanthone-2-carboxylic acid.

36. The composition according to claim 33 in which the compound is the compound wherein $R^6$ is isobutyl; 5-methylthio-7-isobutylxanthone-2-carboxylic acid.

37. The composition according to claim 31 in which the compound is the compound of the formula:

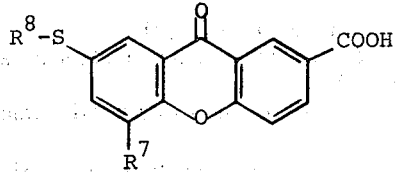

wherein each of $R^7$ and $R^8$ is lower alkyl.

38. The composition according to claim 37 in which the compound is the compound wherein $R^8$ is methyl.

39. The composition according to claim 38 in which the compound is the compound wherein $R^7$ is isopropyl; 5-isopropyl-7-(methylthio)-xanthone-2-carboxylic acid.

40. The composition according to claim 38 in whih the compound is the compound wherein $R^7$ is n-pentyl; 5-n-pentyl-7-(methylthio)-xanthone-2-carboxylic acid.

41. The composition according to claim 38 in which the compound is the compound wherein $R^7$ is isobutyl; 5-isobutyl-7-(methylthio)-xanthone-2-carboxylic acid.

42. The composition according to claim 27 in which the compound is the compound of formula (C).

43. The composition according to claim 42 in which the compound is the compound of the formula:

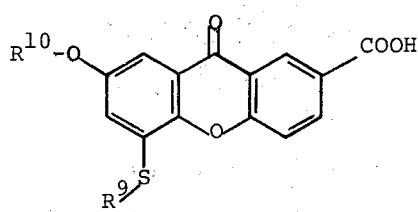

wherein each of $R^9$ and $R^{10}$ is lower alkyl.

44. The composition according to claim 43 in which the compound is the compound wherein $R^9$ is methyl.

45. The composition according to claim 44 in which the compound is the compound wherein $R^{10}$ is isopropyl; 5-methylthio-7-isopropoxyxanthone-2-carboxylic acid.

46. The composition according to claim 42 in which the compound is the compound of the formula:

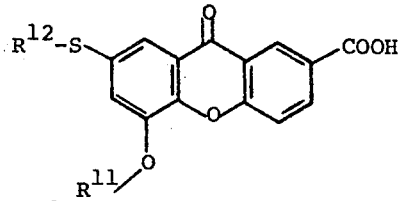

wherein each of $R^{11}$ and $R^{12}$ is lower alkyl.

47. The composition according to claim 46 in which the compound is the compound wherein $R^{12}$ is methyl.

48. The composition according to claim 47 in which the compound is the compound wherein $R^{11}$ is isopropyl; 5-isopropoxy-7-(methylthio)-xanthone-2-carboxylic acid.

49. The composition according to claim 27 in which the compound is the sodium salt compound.

50. The composition according to claim 49 in which the compound is the sodium salt compound of Formula (A).

51. The composition according to claim 49 in which the compound is the sodium salt compound of formula (B).

52. The composition according to claim 49 in which the compound is the sodium salt compound of formula (C).

53. The method according to claim 21 in which the compound is the compound wherein $R^{11}$ is n-pentyl; 5-n-pentyloxy-7-(methylthio)-xanthone-2-carboxylic acid.

54. The method according to claim 21 in which the compound is the compound wherein $R^{11}$ is isopentyl; 5-isopentyl-7-(methylthio)-xanthone-2-carboxylic acid.

55. The composition according to claim 47 in which the compound is the compound wherein $R^{11}$ is n-pentyl; 5-n-pentyloxy-7-(methylthio)-xanthone-2-carboxylic acid.

56. The composition according to claim 47 in which the compound is the compound wherein $R^{11}$ is isopentyl; 5-isopentyl-7-(methylthio)-xanthone-2-carboxylic acid.

* * * * *